United States Patent [19]

Izaka et al.

[11] 4,017,470
[45] Apr. 12, 1977

[54] METHOD FOR PREPARING A HEAT-STABLE PLASMA PROTEIN SOLUTION FROM PASTE IV-1

[75] Inventors: Ken-ichi Izaka, Hirakata; Kazuo Takechi, Sakai, both of Japan

[73] Assignee: The Green Cross Corporation, Osaka, Japan

[22] Filed: June 12, 1974

[21] Appl. No.: 478,884

[30] Foreign Application Priority Data

Feb. 18, 1974 Japan .............................. 49-19247

[52] U.S. Cl. .......................... 260/112 B; 260/122; 424/101
[51] Int. Cl.$^2$ ......................................... C07G 7/00
[58] Field of Search ...................... 260/112 B, 122; 424/101

[56] References Cited

UNITED STATES PATENTS

| | | | |
|---|---|---|---|
| 2,705,230 | 3/1955 | Reid | 260/112 B X |
| 2,761,810 | 9/1956 | Singher et al. | 260/112 B X |
| 2,761,811 | 9/1956 | Kupferberg et al. | 260/112 B X |
| 2,765,299 | 10/1956 | Porsche et al. | 260/112 B X |
| 2,958,628 | 11/1960 | Hink | 260/112 B X |
| 3,100,737 | 8/1963 | Auerswaid et al. | 260/112 B |
| 3,382,227 | 5/1968 | West et al. | 260/112 B |

OTHER PUBLICATIONS

Chem–Abstracts, vol. 80, 1974, Izaka et al. — 874999t, effective date Jan. 17, 1974.
Exp. Immunochemistry, Kabat et al.—pp. 763–765 and 768–773, 1961.

Primary Examiner—Harold D. Anderson
Attorney, Agent, or Firm—Cushman, Darby & Cushman

[57] ABSTRACT

A heat-stable plasma protein solution showing no blood pressure-depressing action is obtained by adding distilled water to a paste IV-1, a waste fraction obtained from the Cohn's cold ethanol plasma fractionation method and has heretofore been discarded as a waste, to extract water-soluble proteins in the paste, heat-treating the extract at pH 4.5 to 5.5 at 50° to 65° C. in the presence of an organic acid to remove as precipitates lipo- and glyco-proteins contained in the extract, adding Rivanol to the resulting supernatant to remove by precipitation residual lipo-proteins giving turbidity to the supernatant, and then removing blood pressure-depressing substances present in the resulting supernatant by adsorption with an inorganic adsorbent or cation exchanger. The thus obtained heat-stable plasma protein solution shows prominent effects in the therapy of shock by acute bleeding, burns, supply of protein nutrients, hypoproteinemia, etc., and is useful for medical treatments.

6 Claims, 4 Drawing Figures

METHOD FOR PREPARING A HEAT-STABLE PLASMA PROTEIN SOLUTION FROM PASTE IV-1

This invention relates to a method for preparing a heat-stable plasma protein solution. More particularly, the invention is concerned with a method for preparing a heat-stable plasma protein solution showing no blood pressure-depressing action by using as starting material a paste IV-1, which is a waste fraction obtained from the Cohn's cold ethanol plasma fractionation method.

Heat-stable plasma protein solutions show prominent effects in the therapy of shock by acute bleeding, burns, supply of protein nutrients, hypoproteinemia, etc., and have been recognized to be useful for medical treatments. As methods for preparing heat-stable protein solutions from plasma, there have been known the following methods:

1. A modification of the Cohn's cold ethanol fractionation method (Japanese Pat. No. 265,704; Japanese Patent Publication No. 5,297/60).
2. A method established by introducing zinc ions into the cold ethanol fractionation method (Douglas M. Surgenor et al.: "Vox Sanguinis", Vol. 5, page 272, 1960).
3. A method in which the ion concentration of plasma is lowered with an ion exchange resin so as to remove unstable globulin by precipitation (Hs. Nitchmann et al.: "Vox Sanguinis", Vol. 1, page 183, 1956).

An object of the present invention is to provide a method for preparing a heat-stable plasma protein solution showing no blood pressure-depressing action by using as starting material a paste IV-1, which is a fraction obtained from the Cohn's cold ethanol plasma fractionation method and discarded as a waste.

Another object of the invention is to provide a heat-stable plasma protein solution showing no blood pressure-depressing action which is markedly effective for the therapy of shock by acute bleeding, burns, supply of protein nutrients, hypoproteinemia, etc.

A further object of the invention is to provide a method for effective utilization of a paste IV-1, which is a waste fraction obtained from the Cohn's cold ethanol plasma fractionation method.

Other objects and advantages of the invention will become apparent from the explanation given below.

In the accompanying drawings.

Figure 1:
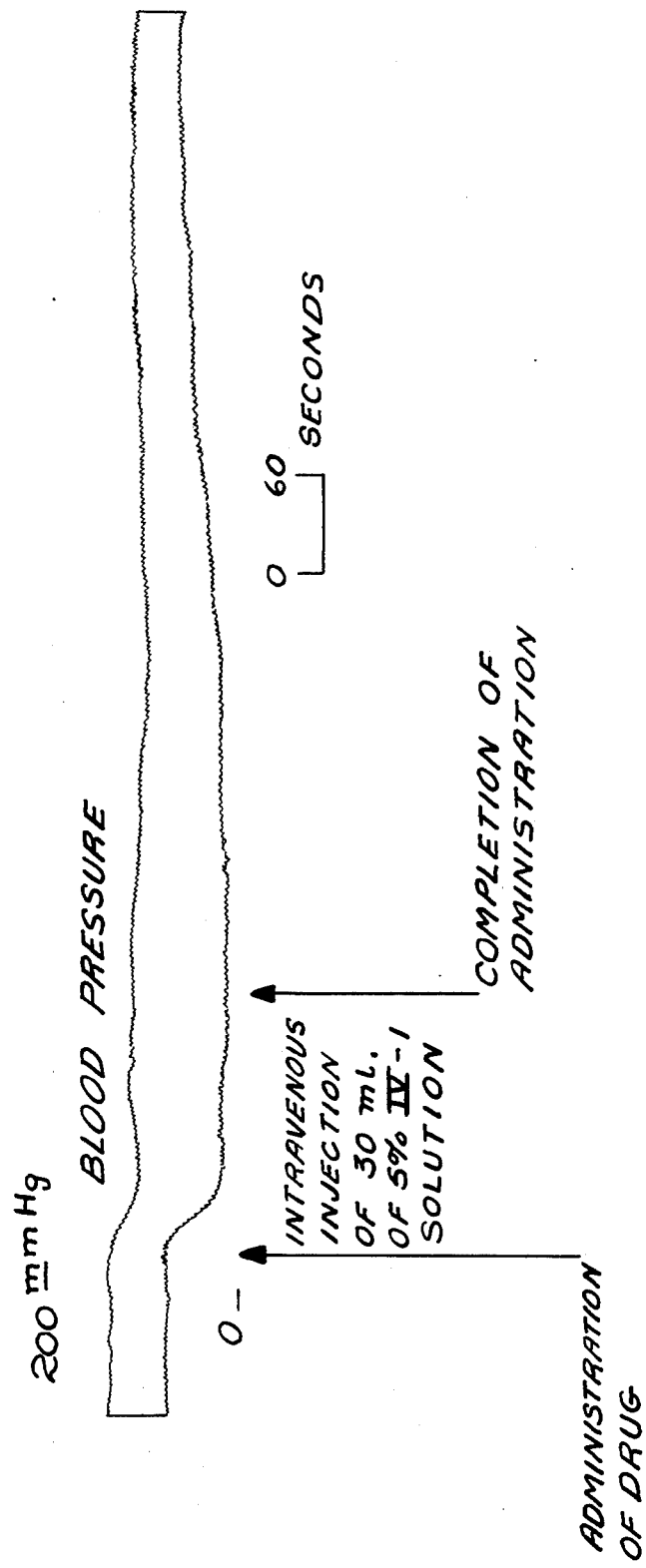
FIG. 1 is a blood pressure curve showing the influence on dog blood pressure of a water extract of the paste IV-1.

Heat-stable plasma protein solutions are ordinarily administered in large doses, and hence are desired to contain no blood-pressure depressing substances derived from plasma.

The paste IV-1 is a fraction formed in the Cohn's cold ethanol plasma fractionation method, but has heretofore been wasted. As detailed in Japanese Patent Publication No. 5,297/60, the paste IV-1 contains such blood pressure-depressing substances as kininogen. Accordingly, when the paste is administered to animals, depression of blood pressure is brought about (refer to FIG. 1). Furthermore, the paste IV-1 contains large quantities of lipo- and glyco-proteins. These proteins are sparingly soluble in water, and hence cannot be constituents of a heat-stable plasma protein solution.

The present inventors made extensive studies on the preparation of heat-stable plasma protein solutions from the aforesaid paste IV-1. As the result, the inventors have found that a major portion of lipo-proteins and glyco-proteins contained in the paste IV-1 can be removed as precipitates by heating the paste in the presence of an organic acid having 4 to 8 carbon atoms, and residual lipo-proteins, which remain in the resulting supernatant to give slight turbidity, can be removed as precipitates by use of Rivanol (2-ethoxy-6,9-diaminoacridine lactate). The inventors have further found that peptide substances showing blood pressure depressing action (and rat uterus smooth muscle contracting action), which are formed during the said heating step from blood pressure-depressing substances such as kininogens contained in the paste IV-1, can be removed by adsorption with an inorganic adsorbent or cation exchanger. The present invention is based on such novel findings as mentioned above. According to the process of the present invention, a heat-stable plasma protein preparation high in medical value and showing no blood pressure-depressing action can first be prepared from the paste IV-1 fraction, which has heretofore been wasted without being utilized. It can therefore be said that the industrial value of the present invention is extremely great.

The present invention is explained in further detail below.

The paste IV-1 used in the present invention is a fraction obtained in the Cohn's cold ethanol plasma fractionation method. Concretely, the said paste is obtained in such a manner that fibrinogen and γ-globulin are removed as precipitates from plasma by addition of alcohol (ethanol) and salts at a low temperature of −3° to −6° C., and then ethanol is added to the supernatant, to a concentration of 19% at pH 5.2 and 6° C. to form a protein precipitate, which is the paste IV-1. Constitutive protein components of the fraction IV-1 are as shown in Table 1.

The thus obtained paste IV-1 is crushed to pieces, and distilled water is added thereto in a proportion of 4 to 10 liters per kg. of the paste. The resulting mixture is sufficiently stirred at 10° to 20° C., and solids contained in the mixture are removed by centrifugation to obtain an extract containing water-soluble proteins. To this extract, a water-soluble organic acid is added to a final concentration of 2 to 6 W/V% (i.e., weight per unit of volume %), and then the extract is subjected to heat treatment.

The above-mentioned organic acid increases the heat stability of albumin, but has no heat stabilization effect on lipo- and glyco-proteins. Accordingly, when the extract is heated at above 50° C., the said proteins can be removed as precipitates. However, if the extract containing the organic acid of such a concentration as above is heated at a temperature higher than 65° C., the albumin also loses its heat stability and is undesirably precipitated together with the lipo- and glyco-proteins. The larger the amount of the organic acid, the greater the proportions of lipo- and glyco-proteins precipitated. However, if the amount of the organic acid is excessively large, the albumin is precipitated together with said proteins in the subseqeunt heating step to lower the yield of the resulting heat-stable plasma protein solution.

The pH of the above-mentioned aqeuous solution is 4.5 to 5.5, preferably 4.9. The heating temperature and times are 50° to 65° C. and 1 to 4 hours, preferably 58° to 60° C. and 1 to 2 hours, respectively. By this heat treatment, the lipo- and glyco-proteins contained in the extract are precipitated. The precipitates are removed by filtration or centrifugation to obtain a supernatant. The supernatant is added with Rivanol in a proportion of 0.2 to 3.0 g/liter, preferably 0.5 to 1.0 g/liter, and then allowed to stand at or below room temperature, whereby residual lipo-proteins, which have been present in the supernatant to provide turbidity, are precipitated. If the proportion of Rivanol is more than 3.0 g/liter, the albumin is also precipitated undesirably. The supernatant is allowed to stand for 2 to 12 hours, preferably 4 to 6 hours, to precipitate the residual lipo-proteins. The precipitate is removed by filtration or centrifugation to obtain a supernatant. This supernatant is treated with an inorganic adsorbent or cation exchanger to remove by adsorption the blood pressure-depressing substances present in the supernatant. The treatment with the inorganic adsorbent or cation exchanger is conducted by charging the adsorbent or exchanger into the supernatant, or by passing the supernatant through a column packed with said adsorbent or exchanger. In the above manner, a heat-stable plasma protein solution containing no blood pressure-depressing substance can be obtained.

The organic acid used in the present invention is an organic acid having 4 to 8 carbon atoms. Concrete examples of the organic acid are butyric, caprylic and mandelic acids. Among these, butyric or mandelic acid is particularly preferable. Examples of the inorganic adsorbent are silica gel and aluminum hydroxide gel. Among these, silica gel is particularly preferable. Examples of the cation exchanger are CM-Sephadex (a cation exchanger composed of dextran having carboxymethyl groups) and CM-Cellulose (a cation exchanger composed of cellulose having carboxymethyl groups). Among these, CM-Sephadex is particularly preferable.

In the Examples shown later, the measurement of blood pressure, smooth muscle contractability, and electrophoresis were effected in the following manner:

1. Measurement of Dog Blood Pressure

A mongrel adult dog (male) of 10 kg. in body weight was anesthetized by administration of urethane, and fixed at its back. A blood vessel cannula was inserted in the left common carotid artery of the dog, and the carotidal pressure thereof was measured through a polygraph transducer. A drug was administered through a catheter inserted in the right thigh-vein. The blood pressure depression of the dog was measured from an average blood pressure before administration of the drug and an average minimum blood pressure after administration of the drug, and calculated according to the following equation:

$$\text{Blood pressure depression rate (\%)} = \frac{\begin{pmatrix}\text{Average blood} \\ \text{pressure before} \\ \text{administration}\end{pmatrix} - \begin{pmatrix}\text{Average blood} \\ \text{pressure after} \\ \text{administration}\end{pmatrix}}{\text{Average blood pressure before administration}} \times 100$$

FIG. 1 is a blood pressure curve observed when 30 ml. of a 5% IV-1 solution was intravenously injected (dose 150 mg/kg, blood pressure depression 47.9%).

Figure 2:
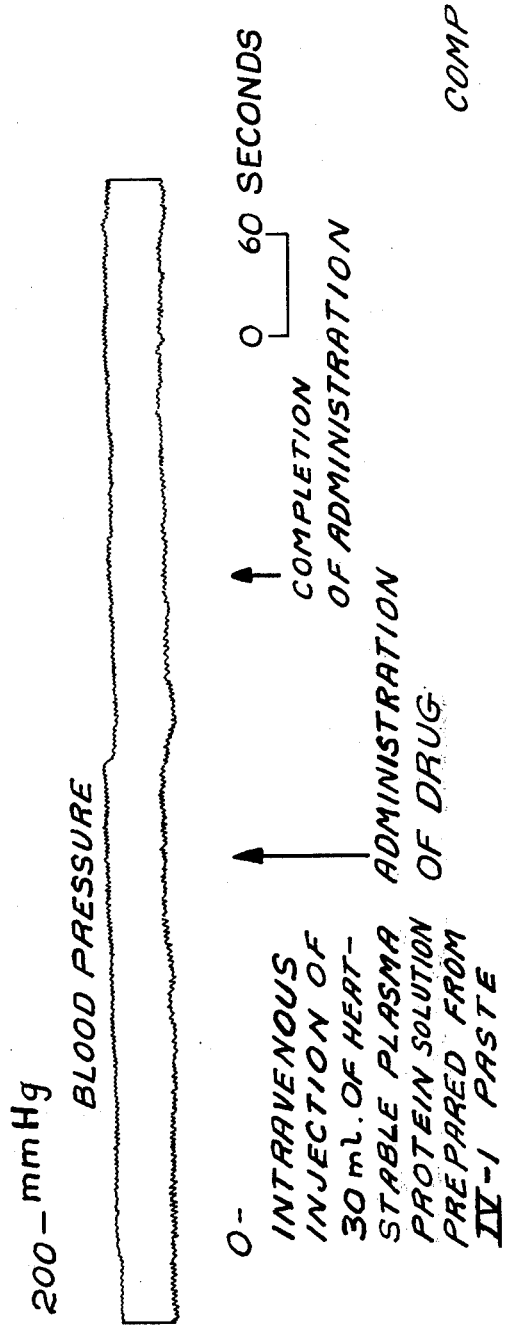
FIG. 2 is a blood pressure curve showing the influence on dog blood pressure of a heat-stable plasma protein solution prepared from the paste IV-1.

FIG. 2 is a blood pressure curve observed when 30 ml. of a 5% heat-stable plasma protein solution prepared from the paste IV-1 was intravenously injected (dose 150 mg/kg, blood pressure depression 4.5%).

Figure 3:
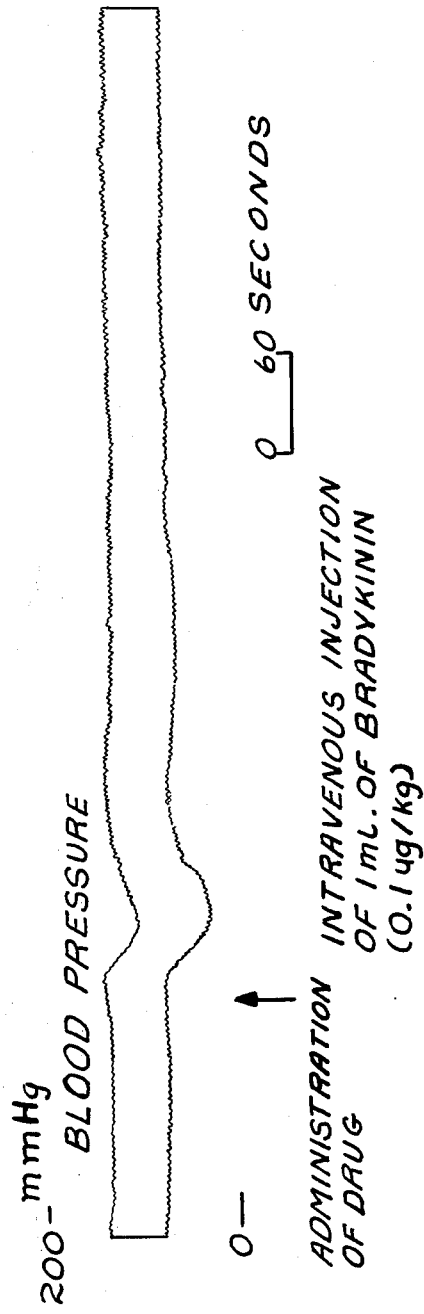
FIG. 3 is a blood pressure curve showing the influence on dog blood pressure of bradykinin used as a control.

FIG. 3 is a blood pressure curve observed when 0.1 μg/kg of bradykinin (control) was intravenously injected (injection volume 1 ml., blood pressure depression 41.1%).

2. Measurement of Rat Uterus Smooth Muscle Contractibility

The measurement was effected according to a modified Magnus method, using the uterus of a virgin rat. That is, 18 hours before uterus isolation, a Wister strain female rat of about 150 g. in body weight was intrapenitoneally administered with 5 mg. of diestradiol, and after 18 hours, the uterus of the rat was isolated and the contractibility of uterus smooth muscle was measured. As the physiological solution was used a de Jalon solution. The volume of the physiological solution in the bath was 8.6 ml., the volume of a sample solution was 0.4 ml., and the reaction time was 90 seconds.

Figure 4:
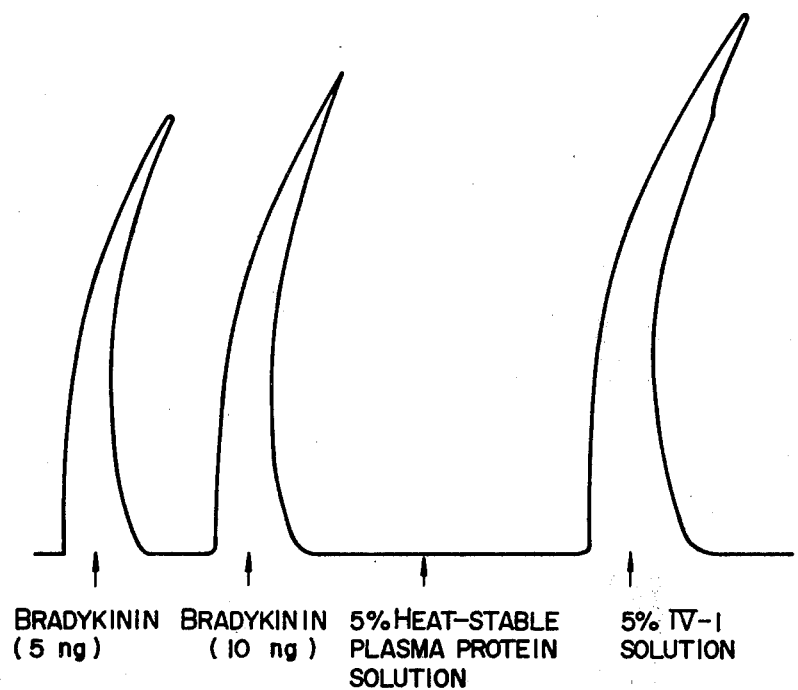
FIG. 4 is a curve showing the rat uterus smooth muscle contractibilities of a water extract of the paste IV-1 and a 5% heat-stable plasma protein solution prepared from said paste.

FIG. 4 shows the rate uterus smooth muscle-contracting actions of a 5% IV-1 solution and a 5% heat-stable plasma protein solution obtained from the paste IV-1. Aqueous solutions containing 5 ng/ml. and 10 ng/ml. of bradykinin were used as controls.

3. Electrophoresis of Proteins

1. Plasma proteins were fractioned according to cellulose acetate electrophoresis (pH 8.6, 0.06μ Veronal buffer solution, 0.6 mA/cm), stained with Ponceau 3R, and then determined by means of a densitometer to measure the percentage of each fractionate. (Reference, Tadashi Kawai and Norio Aoki: "Serum Proteins according to Cellulose Acetate Electrophoresis", page 35, Yatsugi Shoten, Tokyo, 1972).

2. Glyco-proteins were fractionated according to cellulose acetate electrophoresis (pH 8.6, 0.06μ Veronal buffer solution, 0.6 mA/cm), stained according to PAS method (Periodic Acid Schiff's method), and then determined by means of a densitometer to measure the percentage of each fractionate. (Reference, Tadashi Kawai et al.: "Serum Proteins According to Cellulose Acetate Electrophoresis", page 55).

3. Lipo-proteins were fractionated according to paper electrophoresis (pH 8.6, 0.06μ 1% albumin-containing Veronal buffer solution, 200V/20cm), stained with Oil Red, and then determined by means of a densitometer to measure the percentage of each fractionate. (Reference, Robert S. Lees and Frederick T. Hatch: "Sharper Separation of Lipoprotein Species by Paper Electrophoresis in Albumin-Containing Buffer", Journal of Laboratory and Clinical Medicine, Vol. 61, page 518, 1963).

The present invention is illustrated in more detail below with reference to examples, but the examples do not limit the scope of the invention.

EXAMPLE 1

Frozen paste IV-1 was finely crushed and then added to 60 liters of distilled water per 10 kg. of the paste IV-1. The resulting mixture was stirred for 2 hours and then centrifuged, and the supernatant was recovered.

To the supernatant, butyric acid was added to a final concentration of 4%. The supernatant containing butyric acid was adjusted to pH 4.9 and then heated at 57° to 60° C. for 1 hour, and the precipitate formed was separated by filtration. The filtrate was added with 0.2 g. of Rivanol per liter of the filtrate and stirred for 2 hours, and the precipitate formed was separated by centrifugation. The supernatant was added with 3 W/V% of acid clay and stirred for 1 hour to adsorb on the acid clay residual Rivanol present in the supernatant, and then the acid clay was separated by filtration. To filtrate, ammonium sulfate was added to a concentration of 75% to precipitate total proteins. The thus obtained plasma protein paste was dialyzed against water, and the dialyzate was added with 3 W/V% of silica gel and stirred for 1 hour. Thereafter, the silica gel was separated by filtration to obtain a plasma solution composed mainly of albumin.

Plasma proteins in the thus obtained plasma protein solution were examined according to electrophoresis. The proportions of the fractions and the yields of albumin and total protein were shown in Table 1 in comparison with those in the case of the solution at each step and human standard serum. From Table 1, it is understood that the plasma proteins in the heat-stable plasma protein solution obtained in this Example were 95% of albumin and 5% of $\alpha$-globulin. Glyco-proteins in the blood plasma protein solution were also examined according to electrophoresis. The proportions of the fractions and the yield of glyco-proteins were shown in Table 2 in comparison with those in the case of a water extract of paste IV-1 and the standard serum. Likewise, lipo-proteins in the blood plasma protein solution were examined according to electrophoresis. The proportions of the fractions and the yield of lipo-proteins were shown in Table 3 in comparison with those in the case of a water extract of paste IV-1 and the standard serum.

Table 1

Proportions of electrophoretic fractions of plasma proteins in plasma protein solution, and yields of proteins

| Step | Proportions of fractions (%) | | | | Yields of proteins (%) | |
|---|---|---|---|---|---|---|
| | Al | $\alpha$ | $\beta$ | $\gamma$ | Albumin | Total proteins |
| Barbital buffer solution of paste IV-1 | 26 | 67 | 14 | 7 | 100 | 100 |
| Water extract of paste IV-1 | 44 | 24 | 19 | 13 | 81 | 48 |
| Supernatant after butyric acid addition and heat treatment | 93 | 7 | 0 | 0 | 51 | 14 |
| Plasma protein solution obtained | 95 | 5 | 0 | 0 | 47 | 13 |
| Standard serum | 64.5 | 11.0 | 12.5 | 12.0 | — | — |

Note: Al: Albumin; $\alpha$: $\alpha$-Globulin; $\beta$: $\beta$-Globulin; $\gamma$: $\gamma$-Globulin.

Table 2

Proportions of electrophoretic fractions of glyco-proteins in plasma protein solution, and yield of glyco-proteins

| Step | Proportions of fractions (%) | | | | | Yield of glyco-proteins (%) |
|---|---|---|---|---|---|---|
| | Al | $\alpha_1$ | $\alpha_2$ | $\beta$ | $\gamma$ | |
| Water extract of paste IV-1 | 0 | 47 | 31 | 13 | 9 | 100 |
| Plasma protein solution obtained | 0 | 53 | 47 | 0 | 0 | 0.7 |
| Standard serum | 0 | 17.5 | 34.0 | 31.0 | 17.5 | — |

Note: $\alpha_1$: $\alpha_1$-Globulin; $\alpha_2$: $\alpha_2$-Globulin.

Table 3

Proportions of electrophoretic fractions of lipo-proteins in plasma protein solution, and yield of lipo-proteins

| Step | Proportions of fractions (%) | | | | Yield of lipo-proteins (%) |
|---|---|---|---|---|---|
| | Al | $\alpha$ | $\beta$ | $\gamma$ | |
| Water extract of paste IV-1 | 0 | 62 | 38 | 0 | 100 |
| Plasma protein solution obtained | 0 | 0 | 0 | 0 | 0.0 |
| Standard serum | 0 | 35 | 65 | 0 | — |

In order to confirm that the thus obtained heat-stable plasma protein solution showed no blood pressure depressing action, the influence of the solution on dog blood pressure and rat uterus smooth muscle contraction was measured according to the aforesaid methods. As controls, a water extract of the paste IV-1 and bradykinin were also subjected to the same measurement as above. The results obtained were as shown in FIGS. 1, 2, 3 and 4.

As seen in FIG. 1, 1, 30 ml. of a 5% paste IV-1 solution (starting material) was intravenously injected at a constant rate, whereby the blood pressure initiated to depress immediately after administration, the blood pressure depression became maximum after 30 seconds, and the state of blood pressure depression persisted even after completion of administration of the drug. The blood pressure returned to substantially normal 12 minutes after administration of the drug. The blood pressure depression rate was 47.9%.

On the other hand, no significant blood pressure depression was observed when 30 ml. of a 5% heat-stable plasma protein solution prepared from the paste IV-1 was intravenously injected at a constant rate (FIG. 2). Although the blood pressure depression rate was calculated to be 4.5%, a blood pressure depression rate of less than 10% is ordinarily not evaluated as a significant blood pressure depression.

The male adult dog used in the measurement showed a high response to the control synthetic bradykinin (FIG. 3).

Further, as seen in FIG. 4, the 5% heat-stable plasma protein solution showed no action of contracting rat uterus smooth muscle, whereas the 5% paste IV-1 solution showed marked rat uterus smooth muscle contracting action. Thus, it is understood that the 5% heat-stable plasma protein solution contains no blood pressure-depressing substances derived from the paste IV-1 which show dog blood pressure-depressing and rat uterus smooth muscle-contracting actions.

EXAMPLE 2

Frozen paste IV-1 was finely crushed and then added to 70 liters of distilled water per 10 kg. of the paste IV-1. The resulting mixture was stirred for 2 hours and then centrifuged, and the supernatant was recovered. To the supernatant, mandelic acid was added to a final concentration of 5%. Subsequently, the supernatant was adjusted to pH 5.0 and then heated at 58° to 62° C. for 1 hour, and the precipitate formed was separated by filtration. The filtrate was added with 1.0 g. of Rivanol per liter of the filtrate and stirred for 2 hours, and the precipitate formed was separated by centrifugation. The supernatant was added with 3 W/V% of acid clay and stirred for 1 hour, and then the acid clay was separated by filtration. To the filtrate, ammonium sulfate was added to a concentration of 75% to precipitate total proteins. The thus obtained plasma protein paste was dialyzed against water, and the dialyzate was passed through a column packed with pH 7.0-equilibrated CM-Sephadex (a cation exchanger composed of dextran having carboxymethyl groups; produced by Pharmacia Co.), and blood pressure-depressing peptide substances contained in the liquid were removed by adsorption to obtain a heat-stable plasma protein solution. Plasma proteins of the thus obtained solution were examined according to electrophoresis. Proportions of the fractions and yields of the proteins were as shown in Table 4.

Table 4

Proportions of electrophoretic fractions of plasma proteins in the plasma protein solution and yields of proteins

| Step | Proportions of fractions (%) | | | | Yields (%) | |
| --- | --- | --- | --- | --- | --- | --- |
| | Al | α | β | γ | Albumin | Total proteins |
| Barbital buffer soluton of paste IV-1 | 26 | 67 | 14 | 7 | 100 | 100 |
| solution obtained Plasma protein | 93 | 7 | 0 | 0 | 49 | 13.7 |

What is claimed is:

1. A method for preparing a heat-stable plasma protein solution showing no blood pressure-depressing action which comprises adding distilled water to a paste IV-1, a fraction obtained from the Cohn's cold ethanol plasma fractionation method, to extract water-soluble proteins in the paste and removing solids contained in the mixture by centrifuging to obtain an extract containing water-soluble proteins, heat treating the resulting extract at pH 4.5 to 5.5 at 50° to 65° C. with an organic acid having 4 to 8 carbon atoms to a final concentration of the organic acid of 2 to 6 W/V%, removing as precipitates by filtration or centrifugation lipo- and glyco-proteins contained in the extract, adding 2-ethoxy-6,9-diaminoacridine lactate in an amount of 0.2 to 3.0 g. per liter of the supernatant to the resulting supernatant, allowing the mixture to stand at room temperature or below and removing by precipitation residual lipo-proteins giving turbidity to the supernatant, and then removing blood pressure-depressing substances present in the resulting supernatant by adsorption with an inorganic adsorbent or cation exchanger.

2. A method according to claim 1, wherein the organic acid is butyric, caprylic or mandelic acid.

3. A method according to claim 1, wherein the inorganic adsorbent is silica gel or aluminum hydroxide gel.

4. A method according to claim 1 wherein the cation exchanger is dextran having carboxymethyl groups or cellulose having carboxymethyl groups.

5. A method according to claim 1 wherein the amount of 2-ethoxy-6,9-diaminoacridine lactate is 0.5 to 1.0 g per liter of the supernatant.

6. A method according to claim 1 wherein the cation exchanger is detran having carboxymethyl groups.

* * * * *